United States Patent [19]

Blechschmitt et al.

[11] 4,007,136

[45] Feb. 8, 1977

[54] SUPPORTED CATALYST FOR THE OXIDATION OF O-XYLENE AND/OR NAPHTHALENE TO PHTHALIC ANHYDRIDE

[75] Inventors: Kurt Blechschmitt, Schifferstadt; Friedrich Wirth; Paul Hornberger, both of Ludwigshafen; Peter Reuter, Bad Duerkheim; Gert Buerger, Mannheim, all of Germany

[73] Assignee: BASF Aktiengesellschaft, Ludwigshafen (Rhine), Germany

[22] Filed: June 30, 1975

[21] Appl. No.: 591,415

[30] Foreign Application Priority Data

July 26, 1974 Germany .................... 2436009

[52] U.S. Cl. .......................... 252/476; 260/346.4
[51] Int. Cl.² .................. B01J 21/06; B01J 23/04; B01J 23/22
[58] Field of Search .......................... 252/461, 476; 260/346.4

[56] References Cited

UNITED STATES PATENTS

| 1,909,354 | 5/1933 | Jaeger ........................... 260/346.4 |
| 3,464,930 | 9/1969 | Friedrichsen et al. ......... 252/461 X |
| 3,565,829 | 2/1971 | Friedrichsen et al. ......... 252/461 X |

FOREIGN PATENTS OR APPLICATIONS 808,541  6/1974  Belgium ........................... 252/476

*Primary Examiner*—W. J. Shine
*Attorney, Agent, or Firm*—Johnston, Keil, Thompson & Shurtleff

[57] ABSTRACT

Supported catalyst for the oxidation of o-xylene or naphthalene to phthalic anhydride, comprising an inert carrier and the active material applied thereto, which contains from 1 to 40 per cent by weight of vanadium pentoxide, from 60 to 98.84 per cent by weight of titanium dioxide and from 0.16 to 0.6 per cent by weight, based on titanium dioxide, of rubidium in the form of rubidium oxide, the vanadium pentoxide content being from 0.05 to 4 per cent by weight, based on the (complete) catalyst.

1 Claim, No Drawings

SUPPORTED CATALYST FOR THE OXIDATION OF O-XYLENE AND/OR NAPHTHALENE TO PHTHALIC ANHYDRIDE

German Printed Application No. 1,943,759 and German Published Application 2,020,482 disclose catalysts for the oxidation of o-xylene or naphthalene to phthalic anhydride, of which the active material contains alkali metal sulfates in addition to vanadium pentoxide and titanium dioxide. Though these catalysts respectively give yields of 103 and 104 percent by weight of phthalic anhydride, based on o-xylene, it is, from an industrial point of view, desirable to increase these yields further.

The above catalysts have the disadvantage that because of the influence of the alkali metal sulfate they tend to form melts with the vanadium pentoxide, whereby the catalyst loses a part of the vanadium pentoxide.

Belgian Pat. No. 808,541 discloses that supported catalysts containing vanadium pentoxide and titanium dioxide and, in addition, small amounts of sodium and/or potassium in the form of sulfur-free compounds, may be used for the manufacture of phthalic anhydride. The efficiency of these catalysts is not inconsiderable, yields of up to 110 percent by weight of phthalic anhydride, based on o-xylene, being achieved. However, this catalyst, like those described above, has the disadvantage that the said good results are only achievable when using from 40 to 50 g of o-xylene per m$^3$ of air. If more o-xylene, eg. from 60 to 80 g of o-xylene per m$^3$ of air, is used, hot spots form in a narrow zone of the catalyst packing, with temperatures exceeding 500° C. At such high temperatures the catalyst is damaged and the catalyst life therefore considerably reduced. Furthermore, the yield is reduced.

It is an object of the present invention to provide catalysts for the oxidation of o-xylene and/or naphthalene to phthalic anhydride, which permit increasing the amount of o-xylene and/or naphthalene per m$^3$ of air whilst retaining a high yield and long catalyst life.

We have found that this object is achieved with a supported catalyst, suitable for the oxidation of o-xylene and/or naphthalene to phthalic anhydride, comprising an inert non-porous carrier to which is applied a layer of an active material containing from 1 to 40 percent by weight of vanadium pentoxide and from 60 to 98.84 percent by weight of titanium dioxide, the vanadium pentoxide content, based on the (complete) supported catalyst, being from 0.05 to 4 percent by weight, if the catalytic material contains from 0.16 to 0.6 percent by weight of rubidium, based on titanium dioxide in the form of rubidium oxide.

The new catalyst has the advantage that even using up to 150 g of o-xylene per m$^3$ of air, no hot spots which are at above 500° C form. As a result, the catalyst has a long life even using these amounts of o-xylene. Furthermore, a smaller amount of air requires to be compressed when using the new catalysts. Finally, the throughput per unit time for a given catalyst volume can be increased. These advantages are achieved simultaneously with excellent yields.

As an inert non-porous carrier, the new catalysts suitably contain sintered or fused silicates, porcelain, alumina, silicon carbide or quartz. The carried is advantageously in the shape of spheres of diameter from 3 to 12 mm, or in the form of rings.

The catalytic material is applied to the carrier as a layer which is, eg., from 0.04 to 1 mm thick, preferably from 0.05 to 0.2 mm thick. The active material usually accounts for from about 3 to 50 percent by weight of the supported catalyst.

The titanium dioxide used advantageously has an inner surface area of from 3 to 100, preferably from 7 to 50, m$^2$/g and its particle size is advantageously less than 1 $\mu$, eg. from 0.4 to 0.8 $\mu$.

In manufacturing the catalysts, the method followed is, eg., to add the rubidium in the form of the oxide or of some other oxygen-containing compound, eg. the carbonate, acetate or nitrate, to the titanium dioxide. The latter compounds are converted to rubidium oxide at elevated temperatures.

In addition to the constituents mentioned, up to 3 percent by weight, and especially from 0.2 to 1 percent by weight, based on titanium dioxide, of phosphorus in the form of a compound, preferably in the form of phosphoric acid or of phosphorus compounds containing nitrogen, such as ammonium phosphate, can be added to the active material.

The catalytic material advantageously has an inner surface area of from 6 to 90 m$^2$/g, especially from 6 to 20 m$^2$/g. The catalyst may be prepared by conventional methods, eg. by mixing a vanadium compound which is converted to vanadium pentoxide on heating, such as ammonium vanadate or vanadium oxalate, formate, acetate, tartrate or salicylate, in water or an organic solvent, such as formamide, diethylacetamide, ammonium thiocyanate, fused urea or an alkanol, with the finely divided titanium dioxide, with addition of the abovementioned rubidium compounds, and spraying the mixture, which mostly is of pasty consistency, in a coating drum, onto the carrier which has been preheated to from 100° to 450° C. The finely divided titanium dioxide required is obtained by, eg., grinding, advantageously in a colloid mill.

When using the novel supported catalyst for the manufacture of phthalic anhydride, conventional methods may be used for locating the catalyst in, eg., a tube furnace of which the tubes have a diameter of from 18 to 40 mm and a length of from 1 to 4.0 m, and for bringing it into contact with the gaseous mixture of o-xylene and/or naphthalene and air. It is advantageous to use carriers of which the diameter corresponds to about ⅓ of the internal diameter of the tubes used.

The temperature is regulated by surrounding the tubes with a salt melt in which a temperature of from 360° to 450° C is generally maintained. The hourly throughput per liter of catalyst is in general from 1.5 to 6 cubic meters (S.T.P.) of air, charged with up to 150 g, especially from 40 to 100 g, of o-xylene and/or naphthalene per cubic meter (S.T.P.). It is advantageous to preheat the mixture to from 150° to 300° C and then pass it through the tubes; the maximum temperature (hot spot) occurs in the first one-third of the catalyst bed and should not exceed 500° C.

The Examples which follow illustrate the invention.

EXAMPLE 1

1,200 g of steatite rings of external diameter 8 mm, and length 8 mm, are sprayed, in a coating drum, with an aqueous suspension consisting of 400 g of anatase having an inner surface area of 11 m$^2$/g, 73.2 g of vanadyl oxalate (vanadium content, calculated as V$_2$O$_5$, 41% by weight), 500 g of water, 100 g of formamide and 1.46 g of rubidium carbonate at from 120° to 150°

C until the weight of material applied is 12 percent of the weight of the (complete) catalyst.

The catalytic material consists of 0.274% by weight of rubidium oxide (corresponding to 0.25% of Rb), 7.0% by weight of vanadium pentoxide and 92.73% by weight of anatase, corresponding to 1 atom of rubidium per 26.6 atoms of vanadium. Based on anatase, the rubidium content is 0.269%.

An iron tube 3.25 m long and of 25 mm internal diameter is packed to a height of 2.80 m with 1,200 g of this catalyst. The tube is surrounded by a salt melt to regulate its temperature. 4 cubic meters (S.T.P.) of air, charged with about 40 to 60 g of o-xylene of 97 percent by weight purity, per cubic meter (S.T.P.) of air, are passed per hour through the tube. The following results are obtained:

| Amount of o-xylene (g) per cubic meter (S.T.P.) | Temperature (° C) Salt bath | Catalyst bed | Yield |
|---|---|---|---|
| 40.8 | 389 | 450 | 112.1 |
| 61.0 | 385 | 462 | 110.5 |

The "yield" is the amount of phthalic anhydride obtained, in % by weight, based on 100 percent pure o-xylene.

EXAMPLE 2

1,200 g of steatite rings of external diameter 8 mm and length 6 mm are heated to 150° C in a coating drum and sprayed, at from 130° to 150° C, with an aqueous suspension consisting of 400 g of anatase of inner surface area 11 m²/g, 73.2 of vanadyl oxalate (vanadium content, calculated as $V_2O_5$, 41% by weight), 500 g of water, 100 g of formamide and 0.94 g of rubidium carbonate until the weight of the catalytic material applied accounts for 10.0 percent of the total weight of the catalyst.

The catalyst layer consists of 0.17% by weight of rubidium oxide (corresponding to 0.16% by weight of Rb), 7.0% by weight of vanadium pentoxide and 92.83% by weight of anatase, corresponding to 1 atom of rubidium per 41 atoms of vanadium. The rubidium content, based on anatase, is 0.17% by weight.

An iron tube 3.25 m long and of 25 mm internal diameter is packed to a height of 2.80 m with 1,200 g of this catalyst. The iron tube is surrounded by a salt melt to regulate its temperature. 4 cubic meters (S.T.P.) of air, charged with about 40 to 60 g of o-xylene of 97 percent by weight purity, per cubic meter (S.T.P.) of air, are passed per hour through the tube. This gives the results summarized in the table which follows.

| Amount of o-xylene (g) per cubic meter (S.T.P.) of air | Temperature (° C) Salt bath | Catalyst bed | Yield |
|---|---|---|---|
| 39.5 | 385 | 460 | 111.5 |
| 60.0 | 380 | 468 | 110.0 |

EXAMPLE 3

1,200 g of steatite rings of external diameter 8 mm and length 6 mm are sprayed, in a coating drum, with the suspension described in Example 1 which instead of 0.85 g of rubidium carbonate contains 2.30 g of rubidium carbonate, at from 220° to 250° C, until the weight of material applied is 15% of the wieght of the (complete) catalyst.

The catalytic material consists of 0.427% by weight of rubidium oxide (corresponding to 0.39 percent by weight of Rb), 7.0% by weight of vanadium pentoxide and 92.57% by weight of anatase, corresponding to 1 atom of rubidium per 16.8 atoms of vanadium. The rubidium content, based on anatase, is 0.42 percent.

1,200 g of this catalyst are packed to a height of 2.80 m into the iron tube described in Example 1. 4 cubic meters (S.T.P.) of air, charged with about 40, 60 and 70 g of o-xylene of 97 percent by weight purity, per cubic meter (S.T.P.) of air, are passed per hour through the tube. The following results are obtained:

| Amount of o-xylene (g) per cubic meter (S.T.P.) | Temperature (° C Salt bath | Catalyst bed | Yield |
|---|---|---|---|
| 42 | 402 | 480 | 109.5 |
| 58 | 391 | 455 | 109.0 |
| 69 | 385 | 467 | 109.2 |

We claim:
1. A supported catalyst for the oxidation of o-xylene or naphthalene to phthalic anhydride, consisting of an inert nonporous carrier to which has been applied a thin layer of an active material which contains 1 to 40 percent by weight of vanadium pentoxide, and 60 to 98.84 percent by weight of titanium dioxide, and 0.16 to 0.6 percent by weight, based on titanium dioxide, of rubidium in the form of rubidium oxide, and the vanadium pentoxide content, based on supported catalyst, being from 0.05 to 4 percent by weight.

* * * * *